United States Patent [19]
Thompson

[11] Patent Number: 5,628,736
[45] Date of Patent: May 13, 1997

[54] RESILIENT FLUID TRANSPORTING NETWORK FOR USE IN ABSORBENT ARTICLES

[75] Inventor: Hugh A. Thompson, Fairfield, Ohio

[73] Assignee: The Procter & Gamble Company, Cincinnati, Ohio

[21] Appl. No.: 670,282

[22] Filed: Sep. 28, 1995

Related U.S. Application Data

[63] Continuation of Ser. No. 235,580, Apr. 29, 1994, abandoned.

[51] Int. Cl.$^6$ .......................... A61F 13/15; A61F 13/20
[52] U.S. Cl. .................. 604/366; 604/370; 604/378; 604/384; 428/373; 428/311.11; 428/311.51
[58] Field of Search ..................... 604/358, 365–367, 604/370, 378, 384, 385.1; 428/311.1, 311.5, 373, 358

[56] References Cited

U.S. PATENT DOCUMENTS

| | | |
|---|---|---|
| Re. 32,741 | 8/1988 | Miyoshi et al. . |
| 3,092,890 | 6/1963 | Bromley et al. . |
| 3,117,906 | 1/1964 | Tanner . |
| 3,121,040 | 2/1964 | Shaw et al. . |
| 3,156,607 | 11/1964 | Strachan . |
| 3,194,002 | 7/1965 | Raynolds et al. . |
| 3,272,901 | 9/1966 | Sims . |
| 3,295,308 | 1/1967 | Raynolds et al. . |
| 3,340,571 | 9/1967 | Bishop et al. . |
| 3,383,276 | 5/1968 | Gould . |
| 3,492,692 | 2/1970 | Soda et al. . |
| 3,508,390 | 4/1970 | Bagnall et al. . |
| 3,538,208 | 11/1970 | Ohtsuka . |
| 3,613,778 | 10/1971 | Feldman, Jr. . |
| 3,633,538 | 1/1972 | Hoeflin . |
| 3,700,545 | 10/1972 | Matsui et al. . |
| 4,054,709 | 10/1977 | Belitsin et al. . |
| 4,179,259 | 12/1979 | Belitsin et al. . |
| 4,364,998 | 12/1982 | Wei . |

(List continued on next page.)

FOREIGN PATENT DOCUMENTS

| | | |
|---|---|---|
| 0233702 | 8/1987 | European Pat. Off. . |
| 0301874A1 | 2/1989 | European Pat. Off. . |
| 0391814A2 | 10/1990 | European Pat. Off. . |
| 0493728A1 | 7/1992 | European Pat. Off. . |
| 0574772A1 | 12/1993 | European Pat. Off. . |
| 0600331A1 | 6/1994 | European Pat. Off. . |
| 955625 | 1/1950 | France . |
| 63152449 | 8/1974 | Japan . |
| 50-23149 | 2/1975 | Japan . |

(List continued on next page.)

OTHER PUBLICATIONS

"The Fundamentals of Fiber Formation", Andrzej Ziabicki, Wiley–Interscience Publication (New York, 1976), pp. 360–366.

"Man–Made Fibers—Science and Technology", H.F. Mark, et al., vol. 1, pp. 227–231, Interscience Publishers, John Wiley & Sons, Inc., 1967.

Primary Examiner—P. Zuttarelli
Attorney, Agent, or Firm—Kevin C. Johnson; William Scott Andes; E. Kelly Linman

[57] ABSTRACT

The present invention provides a resilient fluid transporting network suitable for use in absorbent articles. The fluid transport network includes a plurality of bicomponent capillary channel fibers capable of intra-fiber fluid transport. The fibers have a base portion and at least two walls extending from the base portion to form an external capillary channel. The walls and the base portion are made of a first polymeric material which has a first melting point temperature. The distal ends of the capillary channel walls are made of a second polymeric material which has a second melting point temperature lower than the first melting point temperature. When heat is applied to the bicomponent fibers at a temperature below the first melting point temperature and above the second melting point temperature the bicomponent fibers bond together at their distal ends to form an interconnected network of capillary channel fibers capable of inter-fiber fluid transfer between the capillary channels of the bonded capillary channel fibers.

20 Claims, 3 Drawing Sheets

U.S. PATENT DOCUMENTS

| | | |
|---|---|---|
| 4,381,325 | 4/1983 | Masuda et al. . |
| 4,405,686 | 9/1983 | Kuroda et al. . |
| 4,406,850 | 9/1983 | Hills . |
| 4,414,276 | 11/1983 | Kiriyama et al. . |
| 4,492,731 | 1/1985 | Bankar et al. . |
| 4,573,986 | 3/1986 | Minetola et al. ............ 604/366 |
| 4,622,054 | 11/1986 | Huey et al. . |
| 4,636,234 | 1/1987 | Huey et al. . |
| 4,668,566 | 5/1987 | Braun . |
| 4,707,409 | 11/1987 | Phillips . |
| 4,710,185 | 12/1987 | Sneyd, Jr. et al. . |
| 4,713,289 | 12/1987 | Shiffler . |
| 4,753,834 | 6/1988 | Braun et al. ............ 604/366 |
| 4,812,361 | 3/1989 | Takemoto et al. . |
| 4,842,792 | 6/1989 | Bagrodia et al. . |
| 4,849,113 | 7/1989 | Hills . |
| 4,908,052 | 3/1990 | Largman et al. . |
| 5,057,368 | 10/1991 | Langman et al. . |
| 5,069,970 | 12/1991 | Langman et al. . |
| 5,141,811 | 8/1992 | Kawakami et al. . |
| 5,162,074 | 11/1992 | Hills . |
| 5,200,248 | 4/1993 | Thompson et al. . |
| 5,231,122 | 7/1993 | Palumbo et al. ............ 604/370 |
| 5,242,644 | 9/1993 | Thompson et al. . |
| 5,268,229 | 12/1993 | Phillips et al. . |
| 5,356,405 | 10/1994 | Thompson et al. ............ 604/370 |

FOREIGN PATENT DOCUMENTS

| | | |
|---|---|---|
| 87001005 | 8/1979 | Japan . |
| 151617 | 11/1979 | Japan . |
| 1026715A | 2/1982 | Japan . |
| 58018430A | 2/1983 | Japan . |
| 61075844 | 9/1984 | Japan . |
| 61083313 | 9/1984 | Japan . |
| 62006933 | 7/1985 | Japan . |
| 62015324 | 7/1985 | Japan . |
| 62028405 | 7/1985 | Japan . |
| 60-259618 | 12/1985 | Japan . |
| 62170510 | 1/1986 | Japan . |
| 62215028 | 3/1986 | Japan . |
| 62238817 | 4/1986 | Japan . |
| 62238818 | 4/1986 | Japan . |
| 62238833 | 4/1986 | Japan . |
| 62238842 | 12/1986 | Japan . |
| 63-295712 | 12/1988 | Japan . |
| 1488676 | 10/1977 | United Kingdom . |
| WO89/02938 | 4/1989 | WIPO . |
| WO93/01780 | 2/1993 | WIPO . |

RESILIENT FLUID TRANSPORTING NETWORK FOR USE IN ABSORBENT ARTICLES

This is a continuation of application Ser. No. 08/235,580, filed on Apr. 29, 1994 now abandoned.

FIELD OF THE INVENTION

The present invention relates to a fluid transporting network suitable for use in absorbent articles, such as sanitary napkins, and more specifically, to a fluid transporting network comprised of a plurality of bicomponent capillary channel fibers which are individually capable of intra-fiber fluid transfer or wicking and which are bonded to one another to form a resilient fluid transporting network capable of inter-fiber fluid transfer between the capillary channels of the bonded capillary channel fibers.

BACKGROUND OF THE INVENTION

A wide variety of structures which absorb and transport body fluids are known in the disposable absorbent article art. Commercial disposable absorbent articles include diapers, adult incontinent products, catamenial pads, and bandages. Disposable products of this type comprise some functional members for accepting, transporting and retaining fluids. Typically, such sanitary napkins, disposable absorbent articles include a fluid-permeable topsheet, an absorbent core and a fluid-impermeable backsheet. In addition, the disposable absorbent articles may include an acquisition layer or secondary topsheet positioned between the topsheet and the absorbent core.

In the case of catamenial pads, users have come to expect a high level of performance in terms of comfort and fit, retention of fluid, and minimal staining and/or soiling of undergarments and clothing. Above all, leakage of fluid from the absorbent article is regarded as totally unacceptable.

In order for a nonwoven material to function well as a fluid transporting member, i.e., as the topsheet, secondary topsheet, or absorbent core on an absorbent article, it is important that the nonwoven material be soft, resilient, and comfortable. In addition, it is desirable if the transporting member is capable of acquiring and transferring fluid within the member itself and to adjacent members and eventually into the absorbent core.

Nonwoven materials formed from capillary channel fibers have been found useful in disposable absorbent articles. These fibers typically hold fluid with higher capillarity (more tightly) than surrounding larger pores. Therefore, it would be desirable to achieve direct, channel-to-channel, or inter-fiber fluid transfer between bonded fibers, holding the fluid more tightly than if the fluid is passed through the large surrounding pores.

Therefore, it is desirable to provide an absorbent article with one or more nonwoven fluid transporting members having the ability to transfer fluids within the member and to adjacent layers or members. It is also desirable to have a fluid transporting member which is soft, resilient, and comfortable to the user.

SUMMARY OF THE INVENTION

The present invention pertains, in a preferred embodiment to a resilient fluid transporting network comprised of a plurality of capillary channel fibers capable of intra-fiber fluid transport. The fibers have a base portion and at least two capillary channel walls extending from the base portion to form an open capillary channel. The capillary channel walls have a base end and a distal end. The base portion and the portion of the capillary channel walls adjacent the base portion are comprised of a first polymeric material having a first melt temperature. The distal ends of the capillary channel walls are comprised of a second polymeric material having a second melt temperature which is lower than that of the first melt temperature such that when heat is applied to the fibers at a temperature below the first melt temperature and above the second melt temperature the fibers bond together at their distal ends to form an interconnected network of capillary channel fibers capable of inter-fiber fluid transfer between the capillary channels of bonded fibers. The network is also capable of resilient recovery from deformation, such as compression and/or tension, without the loss of capillarity.

This network provides a unique combination of low density (for softness, comfort, fit, and fluid acquisition) with the high capillarity of the channels, all with resilience and in-use durability.

Preferably, the first and second polymeric materials are substantially hydrophilic.

The present invention also pertains to an absorbent article. The absorbent article includes a fluid impervious topsheet, a fluid impervious backsheet joined to said topsheet and an absorbent core positioned between the topsheet and the backsheet.

In a preferred embodiment, the absorbent article also includes a fluid transporting network positioned between the topsheet and the absorbent core. The fluid transporting network includes a plurality of bicomponent capillary channel fibers capable of intra-fiber fluid transport.

In another preferred embodiment, the topsheet may be comprised of a plurality of bicomponent capillary channel fibers capable of intra-fiber fluid transport. In addition, the absorbent core may include a fluid transporting network comprised of a plurality of bicomponent capillary channel fibers capable of intra-fiber fluid transport.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify identical elements and wherein:

DETAILED DESCRIPTION OF THE INVENTION

As used herein, the term "absorbent article" refers to devices which absorb and contain body exudates, and, more specifically refers to devices which are placed against or in proximity to the body of the wearer to absorb and contain the various exudates discharged from the body. The term "absorbent article" is intended to include diapers, catamenial pads, sanitary napkins, pantiliners, incontinence pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
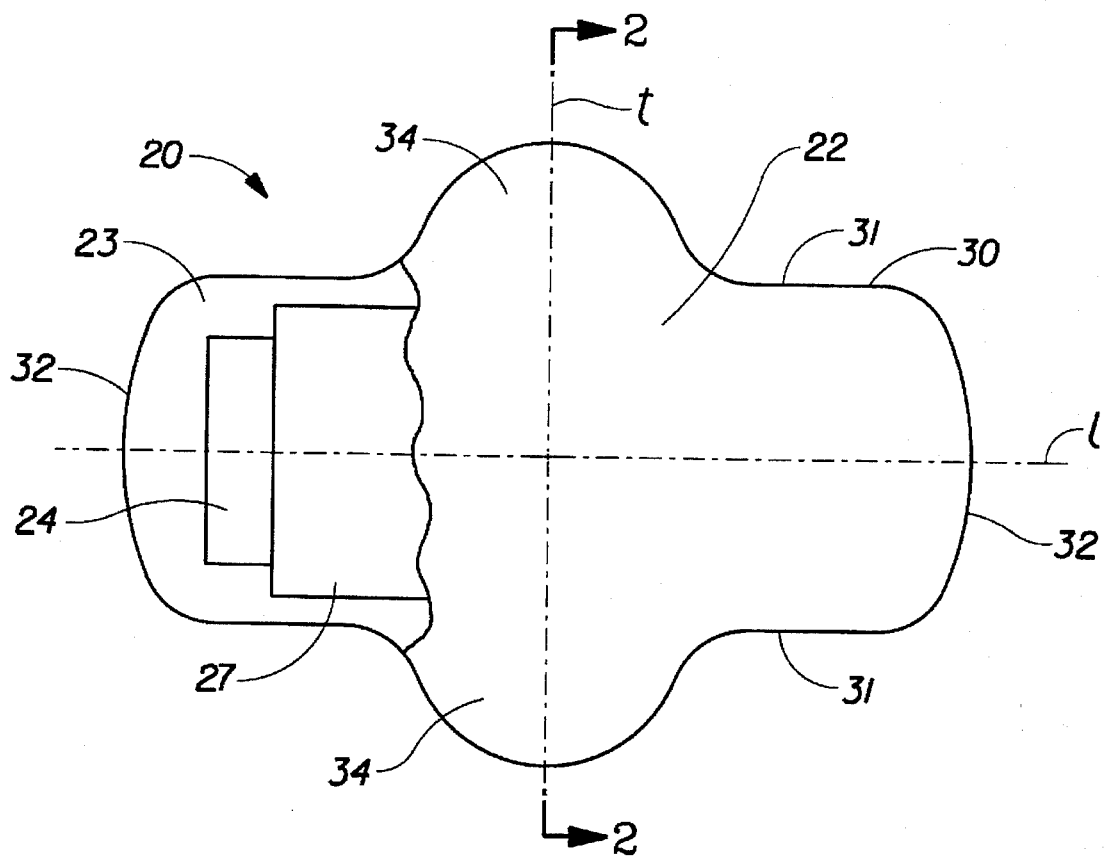
FIG. 1 is a top plan view of a sanitary napkin with portions of the sanitary napkin cut-away to more clearly shown the construction of the sanitary napkin.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region generally external to the urogenital, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 is a top plan view of the sanitary napkin 20 of the present invention in its flat-out state with portions of the structure being cut-away to more clearly shown the construction of the sanitary napkin 20 and with the portion of the sanitary napkin 20 which faces or contacts the wearer 20a oriented towards the viewer. As shown in FIG. 1, sanitary napkin 20 preferably comprises a liquid pervious topsheet 22, and a liquid impervious backsheet 23 joined with the topsheet 22, an absorbent core 24 positioned between the topsheet 22 and the backsheet 23, and a fluid transporting network or secondary topsheet 27 positioned between the topsheet 22 and the absorbent core 24.

FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

Sanitary napkin 20 preferably includes side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

Figure 2:
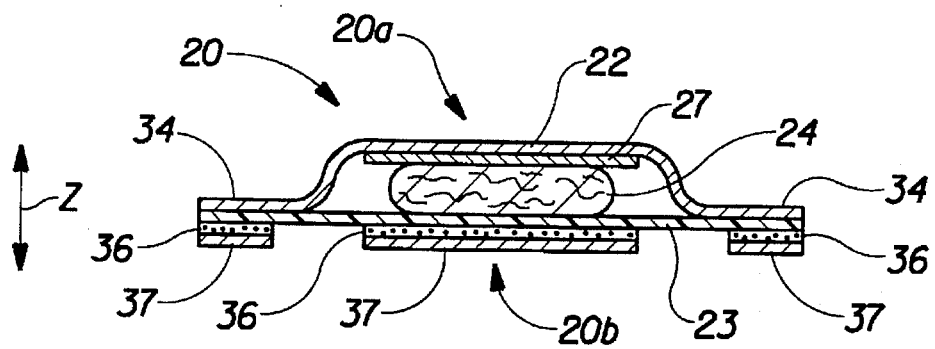
FIG. 2 is a cross-sectional view of the sanitary napkin of FIG. 1 taken along section line 2—2.

FIG. 2 is a cross-sectional view of the sanitary napkin 20 taken along section line 2—2 of FIG. 1. As can be seen in FIG. 2, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

In addition to having a longitudinal direction and a transverse direction, the sanitary napkin 20 also has a "Z" direction or axis, which is the direction proceeding down through the body-contacting layer, e.g., topsheet 22, through the fluid transporting network 27, and into whatever fluid storage means, e.g., absorbent core 24, that may be provided. The objective is to provide a gradient of capillary suction between the topsheet 22 and the fluid transporting network 27 and the absorbent core 24 such that fluid is eventually drawn in the "Z" direction and away from the topsheet of the article into its ultimate storage layer, absorbent core.

The topsheet 22 is compliant, soft feeling, and non-irritating to the wearer's skin. Further, the topsheet 22 is liquid pervious permitting liquids (e.g., menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films, porous foams, reticulated foams, reticulated thermoplastic films, and thermoplastic scrims. Suitable woven and nonwoven materials can be comprised of natural materials (e.g., wood or cotton fibers), synthetic fibers (e.g., polymeric fibers such as polyester, polypropylene, or polyethylene fibers) or from a combination of natural and synthetic fibers.

A preferred topsheet 22 comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 issued to Thompson on Dec. 30, 1975; U.S. Pat. No. 4,324,246 issued to Mullane et al. on Apr. 13, 1982; U.S. Pat. No. 4,342,314 issued to Radel and Thompson on Aug. 3, 1982; U.S. Pat. No. 4,463,045 issued to Ahr on Jul. 31, 1984; U.S. Pat. No. 4,629,643 issued to Curro et al. on Dec. 16, 1986; and U.S. Pat. No. 5,006,394 issued to Baird on Apr. 9, 1991. Each of these patents are incorporated herein by reference. The preferred topsheet 22 for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet 22 is hydrophilic so as to help liquid transfer through the topsheet 22 faster than if the body surface was not hydrophilic. This will diminish the likelihood that menstrual fluid will flow off the topsheet 22 rather than flowing into and being absorbed by the absorbent core 24. In a preferred embodiment, surfactant is incorporated into the polymeric material of the formed film topsheet 22 such as described in U.S. patent application Ser. No. 07/794,745 entitled, "Absorbent Article Having A Nonwoven and Apertured Film Coversheet" filed on Nov. 19, 1991 by Aziz et al. Alternatively, the body surface of the topsheet 22 can be made hydrophilic by treating it with a surfactant such as described in U.S. Pat. No. 4,950,264 issued to Osborn on Aug. 21, 1991 and U.S. Pat. No. 5,009,653 issued to Osborn on Apr. 23, 1991 both of which are incorporated herein by reference.

While the present invention will be described in the context of providing a fluid transporting network suitable for use as a secondary topsheet or an acquisition layer in a disposable absorbent article such as a sanitary napkin, the present invention is in no way limited to such application. To the contrary, the present invention may be practiced to great advantage in many situations where it is desired to transfer fluid from one point to another. For example, the fluid transporting network of the present invention may also be used as a topsheet or an absorbent core in a disposable absorbent article. The detailed description of a preferred structure and its use as a secondary topsheet in a sanitary napkin will allow one skilled in the art to readily adapt the invention to other devices.

Figure 3:
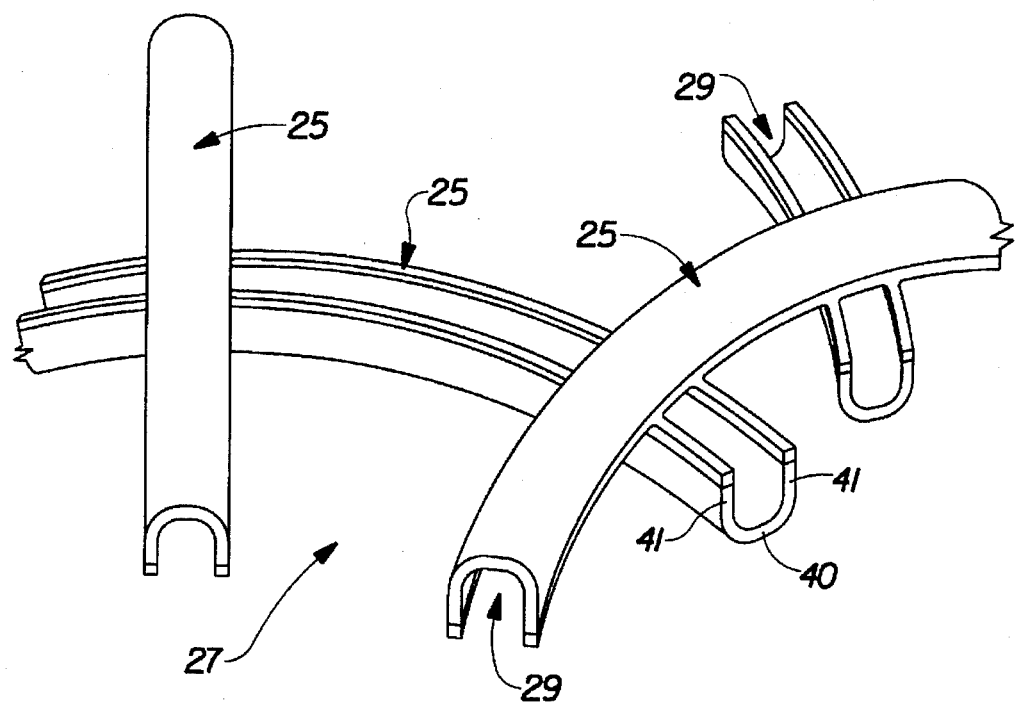
FIG. 3 is an enlarged, segmented perspective illustration of the fluid transporting network of the present invention, the bicomponent capillary channel fibers of the fluid transporting network have a "U"-shaped cross-section.
Figure 4:
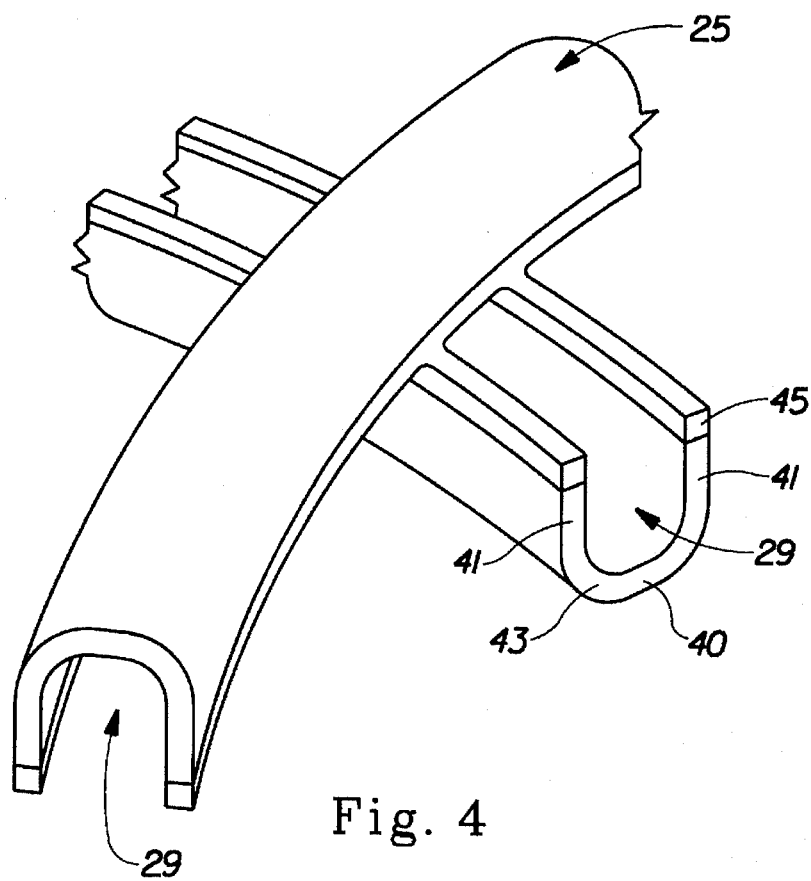
FIG. 4 is a greatly enlarged, segment of the fluid transporting network of FIG. 3, illustrating the intersection of two bicomponent capillary channel fibers.

The fluid transporting network or secondary topsheet 27 transports fluid from the topsheet 22, to the fluid retaining means, i.e., the absorbent core 24. Preferably, the fluid transporting network 27 as seen in FIGS. 3 and 4, is a resilient, three-dimensional, bonded network comprised of a plurality of bicomponent capillary channel fibers 25 having an open capillary channel 29. Although the capillary channel fibers herein may have one capillary channel or a plurality of capillary channels, for convenience the plural form "channels" is used with the intent that it shall refer to a singular "channel" in fibers that can have either one such channel or a plurality of channels as fibers having more than one channel. The fibers are further characterized in that the cross-section of the capillary channels is open along a substantial length of the structure in the axial direction of the channels such that fluid can be received from outside of such channels.

The bicomponent fibers 25 of bonded network 27 have a "U"-shaped cross-section. The fibers 25 have a base portion 40 and at least two capillary channel walls 41 extending from the base portion 40. Base portion 40 and side walls 41 together form an external or open capillary channel 29. Walls 41 have a base end 43 and a distal end 45. The base end 43 of walls 41 is the portion of the wall 41 connected to and adjacent base portion 40. The distal end 45 of walls 41 is that portion of wall 40 opposite of the base end 43.

In a preferred embodiment, the capillary channel walls of the fibers of the present invention are substantially parallel to one another. Substantially parallel, as used herein in reference to cross-sectional parallelism of the walls, means that the alignment differential of adjacent capillary walls is by no more than 40°, preferably by no more than about 30°, and more preferably no more than about 20°. Although not intended to necessarily limit the present invention, substantially parallel walls are believed to provide enhanced capillary fluid movement rate and capillary suction per unit weight of the capillary channel fibers.

The base portion 40 and the walls 41, excluding the distal end 45, of the capillary channel fibers 25 are preferably comprised of a first polymeric material having a first melting point temperature. The distal ends 45 of the capillary channel walls are preferably comprised of a second polymeric material having a second melting point temperature which is lower than the first melting point temperature. As used herein, the term melting point refers to the temperature at the peak of the melting endotherm, at which point the solid and liquid states are in equilibrium. When heat is applied to the fibers at a temperature below the first melting point temperature and above the second melting point temperature the fibers bond together at their distal ends to form an interconnected network of capillary channel fibers capable of inter-fiber fluid transport between the capillary channels of the bonded capillary channel fibers.

Preferably, the individual capillary channel fibers 25 are formed by the coextrusion of two polymers. The polymers used for the base portion 40 and the walls 41 including the distal ends 45 should both be flexible. In addition, the two polymers chosen should have adequate strength to withstand the normal wear and tear expected when used as a fluid transporting network 27 in an absorbent article 20. Furthermore, the polymers should be safe for human contact.

The capillary channel fibers used herein can be prepared from any convenient polymer which is non-swelling when wet. Polymers such as polyethylene, polypropylene, polyester, copolyester, nylon, and the like, are useful herein, so long as they are spinnable such that they can be formed with external capillary channels, as noted herein above. Conveniently, the polymers are melt-extrudable.

The walls and base portion of the fibers may be made from polypropylene having a melting point temperature of about 162° C. The distal ends of the capillary channel fiber may then be made from polyethylene having a melting point temperature of about 131° C. Thus, by heating the capillary channel fibers above 131° C. and below 162° C. the melting point temperature of the distal ends is exceeded, thus allowing the fibers to bond together along their distal ends. Another example of a suitable polymer combination is a fiber having walls and base portion made from polyester (PET) having a melting point of about 250° C. to about 265° C. and the distal ends of the fibers made from copolyester having a melting point of from about 100° C. to about 110° C.

The depth:width ratio of the capillary channels herein is preferably about 2.0, but processing restrictions, as noted above, as well as for economic reasons, a depth:width ratio of greater than about 1.3 is typically employed. Typical and readily producible capillary channel fibers which are quite satisfactory for use herein thus have a depth-of-walls of about 38 microns and a width-between-walls of about 21 microns and a denier per filament of about 15. The walls, themselves, are typically about 3–15 microns thick. Although variations in these dimensions are acceptable, capillary channel fibers prepared from polyesters and having these characteristics are quite effective for their intended purpose. Such fibers can be prepared using convenient operating equipment and readily withstand pressures of the type encountered in sanitary devices, especially sanitary napkins and pantiliners, without collapse or spreading of the capillary channel walls to such an extent that their capillary function is lost.

Generally, bicomponent capillary channel fibers may be made by extrusion as is generally disclosed in commonly assigned U.S. Pat. No. 5,200,248 issued to Thompson et at. on Apr. 6, 1993; and U.S. Pat. No. 5,242,644 issued to Thompson et al. on Sep. 7, 1993 and each of which is hereby incorporated herein by reference combined with bicomponent extrusion techniques generally known to those skilled in the art. The bicomponent fibers may then be cured, cut into staple lengths, air laid, bonded by through-air bonding, and hydrophilized such as by surfactant application. In a through-air bonding process, for example, densification of the web of bicomponent capillary channel fibers may be desirable to promote a sufficient density of channel-to-channel bond sites. Methods such as compaction, pre-embossing, and calendaring are known to those skilled in the art. Separately, it will be appreciated that bonding times and temperatures are adjusted to achieve sufficient softening, melting, and even flow of the low-melt polymer tips such that strong bonds are achieved, yet balancing this with non-clogging of the capillary channels at bond sites.

Typically the bicomponent capillary fiber network 27 may, as one illustration, have the general appearance of a low-density nonwoven fabric. The density may be as low as 0.01 to about 0.02 gm/cc with curled fibers. Microscopically, the bicomponent capillary fiber network is quite open with relatively large inter-fiber pores, as illustrated in FIGS. 3 and 4. Bond sites occur at channel-to-channel fiber intersections. These provide two key functions. First, they create an interconnected network of fine capillaries for fluid handling. Further, these bonds simultaneously create a durable yet soft, highly-resilient structure by eliminating the slippage that otherwise occurs at the fiber contact sites. It will be appreciated that even very infrequent channel-to-channel bonds, separated by many times the fiber width, will create an effective capillary network. Additional bonds for extra non-capillary structural resilience or strength can be achieved by adding low-melt bands on the walls or base of the fibers. Further, the bicomponent nature of the capillary fibers allows good integration with other product layers through bicomponent bonding to the other layers, for example, bonding with the topsheet or absorbent core.

At the bond sites, liquid automatically transfers from one fiber to another. This transfer is valuable not only through allowing more fibers to participate in fluid handling, but because it is accomplished without interruption of the high capillary suction (e.g., 5–20 cm. of water) characteristic of individual capillary channel fibers.

The large inter-fiber pores accept and capture liquid quickly. These pores are then emptied as liquid is wicked away by the interconnected network of fine capillary channels and deposited elsewhere such as in an absorbent core. This structure might be described as "self-draining", since when properly connected to a storage material it empties itself in preparation for the next infusion of fluid.

Figure 5:
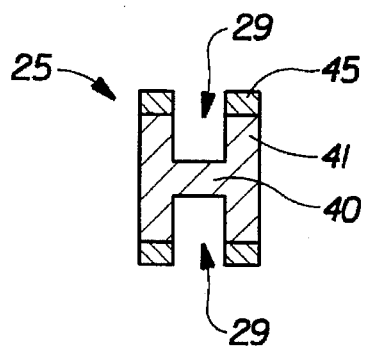
FIG. 5 is a cross-sectional view of an "H"-shaped capillary channel fiber.

The capillary channel fibers can have various shapes to provide particular advantages in certain product applications. For example, the capillary fibers can have a "U"-shaped cross-section as shown in FIG. 3. In addition, the capillary channel fibers can have an "H"-shaped cross-section as shown in FIG. 5. Capillary channel fiber 25 shown in FIG. 5 have two opposing open capillary channels 29 defined by a single base portion 40 and capillary channel walls 41. The base portion 40 and the walls 41, excluding the distal ends 45, are comprised of a first polymeric material having a first melting point temperature. The distal ends of the capillary channel walls are comprised of a second polymeric material having a second melting point temperature which is lower than the first melting point temperature.

Figure 6:
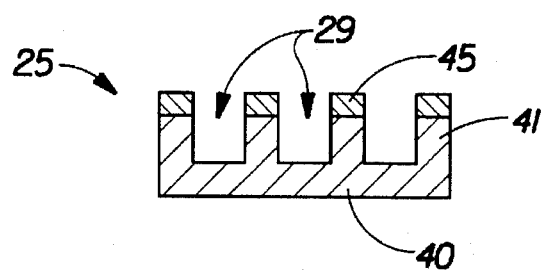
FIG. 6 is a cross-sectional view of a multiple "U"-shaped capillary channel fiber.
Figure 7:
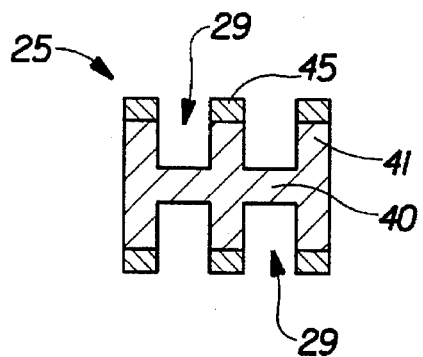
FIG. 7 is a cross-sectional view of a multiple "H"-shaped capillary channel fiber.

FIGS. 6 and 7 are cross-sectional views of other capillary channel fiber shapes that are suitable for use in creating a fluid transporting network. FIG. 6 is an example of a multiple "U"-shaped capillary channel fiber. The multiple "U"-shaped fiber 25 has a single base portion 40 with a plurality of walls 41 extending therefrom. The walls 41 are made of a first polymeric material having a first melting point temperature while the distal ends 45 are made from a second polymeric material having a second melting point temperature which is lower than the first melting point temperature. FIG. 7 is an example of a multiple "H"-shaped capillary channel fiber. The multiple "H"-shaped fiber 25 has a single base portion 40 with a plurality of walls 41 extending therefrom. The walls 41 are made of a first polymeric material having a first melting point temperature and the distal ends 45 are made of a second polymeric material having a second melting point temperature which is lower than the first melting point temperature.

Figure 8:
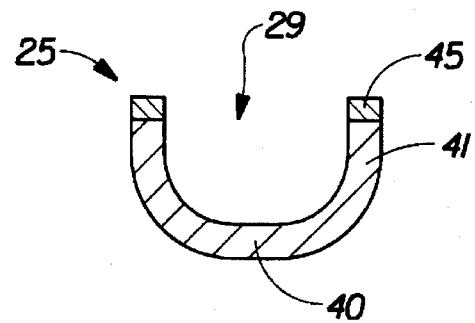
FIG. 8 is a cross-sectional view of a "C"-shaped capillary channel fiber.

FIG. 8 is a cross-sectional view of another capillary channel fiber 25 having a "C"-shaped cross-section. The fiber 25 is defined by a single base portion 40 and walls 41. The base portion 40 and the walls 41, excluding the distal ends 45 are comprised of a first polymeric material having a first melting point temperature. The distal ends are comprised of a second polymeric material having a second melting point temperature which is lower than the first melting point temperature.

The absorbent core 24 may be any absorbent means which is capable of absorbing and retaining liquids (e.g., menses and/or urine) against capillary suction. As shown in FIGS. 1 and 2, the absorbent core 24 has a body surface, a garment surface, side edges, and end edges. The absorbent core 24 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials, or any equivalent material or combinations of materials, or mixtures of these provided they absorb and retain liquids against capillary suction.

The configuration and construction of the absorbent core 24 may also be varied (e.g., the absorbent core may have varying caliper zones, or may have profiling so as to be thicker in the center), hydrophilic gradients, super absorbent gradients, or may comprise of one or more layers or structures. The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular sanitary napkins, or overnight sanitary napkins.

Exemplary absorbent structures for use as the absorbent core 24 of the present invention are described in U.S. Pat.

No. 4,950,264 issued to Osborn on Aug. 21, 1990; U.S. Pat. No. 4,610,678 issued to Weisman et at. on Sep. 9, 1986; U.S. Pat. No. 4,834,735 issued to Alemany et at. on May 30, 1989; U.S. Pat. No. 5,009,653 issued to Osborn on Apr. 23, 1991; and European Patent Application 0 198 683, The Procter & Gamble Company, published Oct. 22, 1986 in the name of Duenk et al. Each of these patents are incorporated herein by reference. Another exemplary absorbent structure for use as the absorbent core 24 of the present invention is described in U.S. patent application entitled, "Absorbent Core for Use in Catamenial Products", Ser. No. 07/734,405, filed Jul. 23, 1991, inventors Buenger et al.

The absorbent core 24 may be comprised of a laminate structure including a layer of superabsorbent polymeric (or absorbent gelling material) in one or more sheets or webs of cross-linked cellulosic fibers. Alternatively, the absorbent core 24, may comprise a single sheet of cross-linked cellulosic fibers. Suitable cross-linked cellulosic fibers for use in the absorbent core 24 are described in U.S. Pat. No. 4,888,093 issued to Cook et at. on Dec. 19, 1989; U.S. Pat. No. 4,822,543 issued to Dean on Apr. 18, 1989; U.S. Pat. No. 4,889,595 issued to Schoggen et al. on Dec. 26, 1989; U.S. Pat. No. 4,898,642 issued to Moore et al. on Feb. 6, 1990; U.S. Pat. No. 4,935,022 issued Jun. 19, 1990 to Lash et al.; EPO Patent Application Publication Nos. 0 427 316 A2 and 0 427 317 A2 published in the name of Herron et at. on May 15, 1991; and EPO Patent Application Publication No. 0 429 112 A2 published in the name of Herron et al. on May 29, 1991. All of the above being incorporated herein by reference.

The cross-linked cellulosic fibers may be in the form of a sheet that wraps the layers of particles of absorbent gelling material. In this type of core, curled, twisted, preferably chemically stiffened and cross-linked, cellulose fibers are refined to provide fibers which can be used in sheet form as the absorbent core. The preparation of suitable curled, chemically stiffened cellulosic fibers from which one can prepare the refined, curled, chemical stiffened cellulosic fibers are described in detail in U.S. Pat. Nos. 4,888,903; 4,822,543; 4,889,595, 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as cross-linking agents. In addition, polycarboxylic acids can be used as cross-linking agents. It will be appreciated that other means for preparing other cross-linked cellulosic fibers are also known, and such fibers may also be used herein, although the fluid absorbency properties may be suboptimal as compared with the above-mentioned fibers. Reference can be made to the various citations in the U.S. Pat. No. 4,898,642 and PCT U.S. 89 01581 for other fiber types. Once in hand, the cellulosic fibers are refined to provide the fibers used to prepare the preferred absorbent cores used in the practices of this invention.

Preferably, in order to provide sustained fluid transport in the fluid transporting network 27 the absorbent core 24 has certain performance characteristics such as capillary suction, and fluid retention capacity. Preferably, the capillary suction of the absorbent core 24 should be greater than that of the capillary channel fibers 25 of the fluid transporting network 27. Preferably, the fluid retention capacity of the absorbent core 24 is at least 5 g/g. The above performance characteristics are typically achieved in an absorbent core having a density of about 0.1 g/cc to about 0.2/cc.

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents exudates absorbed and contained in the absorbent core 24 from wetting articles which contact the sanitary napkin 20 such as pants, pajamas, and undergarments. The backsheet 23 may thus comprise a woven or nonwoven material, polymeric film such as thermoplastic films of polyethylene or polypropylene, or composite material such as a film-coated nonwoven material. Preferably, the backsheet is a polyethylene film having a thickness from about 0.012 mm (0.5 mil) to about 0.051 mm (2.0 mils). Exemplary polyethylene films are manufactured by Clopay Corporation of Cincinnati, Ohio, under the designation P 18-0401 and by Ethyl Corporation, Visqueen Division, of Terre Haute, Ind., under the designation XP-39385. The backsheet 23 is preferably embossed and/or matte finish to provide a more clothlike appearance. Further, the backsheet 23 may permit vapors to escape from the absorbent core 24 (i.e., breathable) while still preventing exudates from passing through the backsheet 23.

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. thus, a portion or all of the outer surface of the backsheet 23 is coated with adhesive. Any adhesive or glue used in the art for such purposes can be used for the adhesive herein with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out and/or adhering to a surface other than the crotch portion of the panty prior to use. Suitable release liners 37 are also described in the above-referenced U.S. Pat. No. 4,917,697. Any commercially available release liners, used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

While particular embodiments of the present invention have been illustrated and described, it would be obvious to those skilled in the art that various other changes and modifications can be made without departing form the spirit and scope of the present invention. It is therefore intended to cover in the appended claims all such changes and modifications that are within the scope of this invention.

What is claimed is:

1. A resilient fluid transporting network comprised of a plurality of bicomponent capillary channel fibers capable of intra-fiber fluid transport, said fibers having a base portion and at least two capillary channel walls extending from said base portion forming an open capillary channel, said capillary channel walls having a base end and a distal end, said capillary channel walls and said base portion being comprised of a first polymeric material having a first melting point temperature, said distal ends of said capillary channel walls being comprised of a second polymeric material having a second melting point temperature which is lower than said first melting point temperature, such that when heat is applied to said fibers, at a temperature below said first melting point temperature and above said second melting point temperature, distal ends of said fibers bond together at channel-to-channel fiber intersections to form an interconnected network of capillary channel fibers capable of inter-fiber fluid transfer between the capillary channels of bonded capillary channel fibers, wherein said capillary channel walls are substantially parallel to each other.

2. The fluid transporting network of claim 1, wherein said first and second polymeric materials are substantially hydrophilic.

3. The fluid transporting network of claim 1, wherein said network is resilient in compression and in tension.

4. The fluid transporting network of claim 1, wherein said fluid transporting network is a secondary topsheet in an absorbent article.

5. The fluid transporting network of claim 1, wherein said fluid transporting network is a topsheet in an absorbent article.

6. The fluid transporting network of claim 1, wherein said fluid transporting network is an absorbent core in an absorbent article.

7. The fluid transporting network of claim 1, wherein said capillary channel fibers have a U-shaped cross-section.

8. The fluid transporting network of claim 1, wherein said capillary channel fibers have a multiple U-shaped cross-section.

9. The fluid transporting network of claim 1, wherein said capillary channel fibers have an H-shaped cross-section.

10. The fluid transporting network of claim 1, wherein said capillary channel fibers are substantially curled.

11. An absorbent article comprising:
   (a) a fluid pervious topsheet;
   (b) a fluid impervious backsheet joined to said topsheet;
   (c) an absorbent core positioned between said topsheet and said backsheet; and
   (d) a fluid transporting network positioned between said topsheet and said absorbent core, said fluid transporting network including a plurality of bicomponent capillary channel fibers capable of intra-fiber fluid transport, said fibers having a base portion and at least two capillary channel walls extending from said base portion forming an open capillary channel, said capillary channel walls having a base end and a distal end, said capillary channel walls and said base portion being comprised of a first polymeric material having a first melting point temperature, said distal ends of said capillary channel walls being comprised of a second polymeric material having a second melting point temperature which is lower than said first melting point temperature, such that when heat is applied to said fibers, at a temperature below said first melting point temperature and above said second melting point temperature, distal ends of said fibers bond together at channel-to-channel fiber intersections to form an interconnected network of capillary channel fibers capable of inter-fiber fluid transfer between the capillary channels of bonded capillary channel fibers, wherein the capillary channel walls are substantially parallel to one another.

12. The absorbent article of claim 11, wherein said first and second polymeric materials are substantially hydrophilic.

13. The absorbent article of claim 11, wherein said network is resilient in compression and in tension.

14. The absorbent article of claim 11, wherein said absorbent article is a sanitary napkin.

15. The absorbent article of claim 11, wherein said capillary channel fibers are substantially curled.

16. An absorbent article comprising:
   (a) a fluid pervious topsheet, said topsheet including a plurality of bicomponent capillary channel fibers capable of intra-fiber fluid transport, said fibers having a base portion and at least two capillary channel walls extending from said base portion forming an open capillary channel, said capillary channel walls having a base end and a distal end, said capillary channel walls and said base portion being comprised of a first polymeric material having a first melting point temperature, said distal ends of said capillary channel walls being comprised of a second polymeric material having a second melting point temperature which is lower than said first melting point temperature, such that when heat is applied to said fibers, at a temperature below said first melting point temperature and above said second melting point temperature, distal ends of said fibers bond together at channel-to-channel fiber intersections to form an interconnected network of capillary channel fibers capable of inter-fiber fluid transfer between the capillary channels of bonded capillary channel fibers, wherein the capillary channel walls are substantially parallel to one another;
   (b) a fluid impervious backsheet joined to said topsheet; and
   (c) an absorbent core positioned between said topsheet and said backsheet.

17. The absorbent article of claim 16, wherein said first and second polymeric materials are substantially hydrophilic.

18. The absorbent article of claim 16, wherein said network is resilient in compression and in tension.

19. The absorbent article of claim 16, wherein said absorbent article is a sanitary napkin.

20. The absorbent article of claim 16, wherein said capillary channel fibers are substantially curled.

* * * * *